US011291236B2

(12) United States Patent
First et al.

(10) Patent No.: US 11,291,236 B2
(45) Date of Patent: Apr. 5, 2022

(54) DEVICES AND METHODS FOR THE PREPARATION OF A NUTRITIONAL FORMULA

(71) Applicant: Alcresta Therapeutics, Inc., Newton, MA (US)

(72) Inventors: Eric First, Morristown, NJ (US); David Brown, Brookline, MA (US); Albert Archie Stone, Fuquay-Varina, NC (US)

(73) Assignee: Alcresta Therapeutics, Inc., Newton, MA (US)

( * ) Notice: Subject to any disclaimer, the term of this patent is extended or adjusted under 35 U.S.C. 154(b) by 829 days.

(21) Appl. No.: 16/123,712

(22) Filed: Sep. 6, 2018

(65) Prior Publication Data

US 2019/0075830 A1 Mar. 14, 2019

Related U.S. Application Data

(60) Provisional application No. 62/643,394, filed on Mar. 15, 2018, provisional application No. 62/556,700, filed on Sep. 11, 2017.

(51) Int. Cl.
| | | |
|---|---|---|
| *A61J 15/00* | (2006.01) | |
| *A23L 29/00* | (2016.01) | |
| *A61K 38/46* | (2006.01) | |
| *C12N 9/50* | (2006.01) | |
| *C12N 9/26* | (2006.01) | |
| *A61K 38/48* | (2006.01) | |
| *A61K 38/47* | (2006.01) | |
| *C12N 9/20* | (2006.01) | |
| *A23L 33/12* | (2016.01) | |
| *A61K 9/00* | (2006.01) | |

(Continued)

(52) U.S. Cl.
CPC .............. *A23L 29/06* (2016.08); *A23L 33/12* (2016.08); *A61J 15/0026* (2013.01); *A61J 15/0076* (2015.05); *A61J 15/0092* (2013.01); *A61K 38/465* (2013.01); *A61K 38/47* (2013.01); *A61K 38/48* (2013.01); *C12N 9/20* (2013.01); *C12N 9/2411* (2013.01); *C12N 9/50* (2013.01); *C12Y 301/01003* (2013.01); *C12Y 302/01001* (2013.01); *C12Y 304/00* (2013.01); *A23L 33/40* (2016.08); *A61J 3/002* (2013.01); *A61K 9/0029* (2013.01); *A61M 5/142* (2013.01); *A61M 5/1409* (2013.01); *A61M 5/16827* (2013.01)

(58) Field of Classification Search
CPC .......................... A61M 5/1409; A61J 15/0026
See application file for complete search history.

(56) References Cited

U.S. PATENT DOCUMENTS

| 9,668,942 B2 | 6/2017 | Margolin et al. | |
|---|---|---|---|
| 2010/0239559 A1* | 9/2010 | Freedman | A61P 1/14 424/94.61 |

(Continued)

FOREIGN PATENT DOCUMENTS

WO    WO 2015/020943 A2    2/2015

*Primary Examiner* — Jenna Zhang
(74) *Attorney, Agent, or Firm* — Bookoff McAndrews, PLLC (57) ABSTRACT

Exemplary embodiments of the disclosure may be drawn to a device having an inlet and a chamber. Immobilized lipase, immobilized protease, and immobilized amylase may be contained within the chamber. The device may also include an outlet, wherein a flow path extends from the inlet, through the chamber, and to the outlet.

20 Claims, 4 Drawing Sheets

(51) Int. Cl.
*A61M 5/142* (2006.01)
*A61M 5/14* (2006.01)
*A61M 5/168* (2006.01)
*A23L 33/00* (2016.01)
*A61J 3/00* (2006.01)

(56) References Cited

U.S. PATENT DOCUMENTS

2015/0246102 A1\* 9/2015 Margolin ............... A23D 9/013
 424/94.6
2017/0105903 A1\* 4/2017 Gallotto ................. C12N 11/06

\* cited by examiner

DEVICES AND METHODS FOR THE PREPARATION OF A NUTRITIONAL FORMULA

CROSS-REFERENCE TO RELATED APPLICATIONS

This application claims the benefits of priority from U.S. Provisional Application No. 62/556,700, filed on Sep. 11, 2017, and U.S. Provisional Application No. 62/643,394, filed on Mar. 15, 2018, the entireties of each of which are incorporated herein by reference.

FIELD OF THE DISCLOSURE

Embodiments of the present disclosure are directed to devices and methods for preparing and/or supplementing a nutritional formula, and more particularly, to devices and methods for exposing a nutritional formula to lipase, protease, and/or amylase to hydrolyze fats, proteins, and/or carbohydrates, respectively, prior to administering the nutritional formula to a subject.

BACKGROUND

Long-chain fatty acids are important to human health and development. Many long-chain fatty acids are consumed as triglycerides, in which three long-chain fatty acids are bound to a glycerol molecule via ester linkages. Absorption of long-chain triglycerides (LCTs) by the body first requires the enzymatic action of lipases (e.g. pancreatic lipase) and bile salts, which digest triglycerides through hydrolysis, breaking them down into a monoglyceride and two free fatty acids. Digestion products consisting of a mixture of glycerol, tri-, di-, and monoglycerides and free fatty acids, which, together with the other fat soluble contents of the diet (e.g. the fat soluble vitamins and cholesterol) and bile salts, form mixed micelles in the watery duodenal contents. Once broken down, the monoglycerides and free fatty acids may be absorbed by enterocytes—epithelial cells lining the small intestine—for example, in the region of the jejunum. The contents of these micelles (but not the bile salts) enter the enterocytes, where they are resynthesized into triglycerides and packaged into chylomicrons, which are released into the lacteals (the capillaries of the lymph system of the intestines). Medium-chain triglycerides (MCTs) are absorbed directly into the bloodstream.

The breakdown of proteins is a fundamental part of the human digestive system. A protease is an enzyme that breaks down proteins by hydrolyzing one or more peptide bonds in a protein or peptide. The human digestive track produces a number of proteases, such as pepsin, trypsin, and chymotrypsin. In the stomach of the human body, the inactive enzyme pepsinogen is produced and reacts into pepsin when it contacts the acid environment of the stomach. Pepsin breaks apart proteins, producing smaller peptides and beginning protein digestion. The pancreas makes trypsin and chymotrypsin, protease enzymes that are released into the small intestine through the pancreatic duct. When partially digested food moves from the stomach into the intestine, trypsin and chymotrypsin complete protein digestion, producing simple amino acids that are absorbed into the blood stream. The breakdown of proteins through protease enzymes is vital for a properly functioning digestive system.

Carbohydrates in food are an important and immediate source of energy for the human body. Carbohydrates may be stored in the body as glycogen for future use. When carbohydrates are not properly broken down before they are absorbed into the blood stream, adverse health consequences may occur. Amylase enzymes are enzymes that break down carbohydrates, such as sugar and starch. Amylase enzymes are found in saliva, and as soon as a subject begins to chew food, amylase enzymes are secreted by the mouth. The pancreas also produces the amylase enzymes that are released into the duodenum of the small intestines. Amylase enzymes digest polysaccharides into smaller disaccharide units, eventually converting them into monosaccharides, such as glucose, and completing the digestion of carbohydrates.

Exocrine pancreatic function may not be fully developed at birth in premature infants, and so premature infants may lack sufficient quantities of the enzymes lipase, protease, and/or amylase, which are necessary to break down triglycerides, proteins, and carbohydrates, respectively. A mother's breast milk provides on-board digestive enzymes to help an infant digest triglycerides, proteins, and carbohydrates. For example, at birth, the mother provides an "on-board lipase," called bile salt-stimulated lipase (BSSL), also known as carboxyl ester lipase or bile salt-dependent lipase, which is provided to the infant through breast milk. While this may partially compensate for poor endogenous production, BSSL production may be insufficient for supporting proper fat absorption, e.g., in the case of preterm birth. Additionally, the majority of fats in mother's milk are in the form of palmitic acid (n−16), which is an MCT, and thus mother's milk may lack sufficient LCTs, e.g., those containing docosahexaenoic acid (DHA, 22:6 n−3) and arachidonic acid (ARA 20:4 n−6), which are critical in membrane structure, function, and neuronal, retinal, and other tissue development. In donor milk, during the pasteurization process, lipase that was present may be inactivated by exposure to high heat, and thus LCT fats are not as readily broken down. As a result, an infant may suffer from feeding intolerance due to the inability to absorb these larger LCTs, irritating the gut mucosa and initiating localized inflammation.

Human milk may not meet the high daily nutrient requirements of a very low body weight infant and/or may contain nutrients in forms that an immature or deficient GI system may not be able to process. For example, standard fortification of human milk designed to optimize nutritional intake often falls short of the nutrient requirements with regard to protein, fats, and carbohydrates. This problem may be further amplified with the use of donor milk, which is often donated by the mothers of term infants beyond 1 month postpartum, and which is likely to have lower protein and fat content than preterm mothers' milk.

The fat and protein content of human milk is extremely variable, and protein decreases with lactation duration. In recent years, it has become evident that preterm infants fed fortified human milk (mother's milk or donor milk) receive less protein than assumed and continue to grow more slowly in the short term, even with standard human milk fortification. Although there is some uncertainty about optimal growth, postnatal growth failure has not been solved with human milk fortification in standard fashion. Thus, there is a need for improved fortification of human milk to achieve better short-term infant growth, which is associated with improved neurocognitive outcomes, among other improvements. The ability to more efficiently process and absorb LCTs, proteins, and carbohydrates may lead to better overall nutrient absorption and thus growth.

For at least the above reasons, current infant nutritional formula (including mother's milk, donor milk, infant formula, and/or fortifiers) may lack sufficient nutrient density for premature infants and/or infants may be unable to absorb the nutrients provided in the nutritional formula. Accordingly, methods and devices to increase the bioavailability of nutrients in nutritional formula, and/or increase nutrient density in nutritional formula for premature infants are needed. Further, patients suffering from various malabsorption impairments may be unable to adequately digest proteins, carbohydrates, and/or fats, LCTs and other forms of fat through hydrolysis, inhibiting absorption of the proteins, carbohydrates, and/or fatty acids required to maintain health. Exemplary impairments include, but are not limited to, the following: compromised pancreatic output, acute and chronic pancreatitis, pancreatic cancer, pancreatic insufficiency, cystic fibrosis, cerebral palsy, Crohn's disease, irritable bowel syndrome, chronically abnormal epithelium, amyloidosis, celiac disease, ischemia, radiation enteritis, tropical sprue, Whipple disease, inadequate gastric mixing, rapid emptying, or both, Billroth II gastrectomy, gastrocolic fistula, gastroenterostomy, insufficient digestive agents, biliary obstruction and cholestasis, cirrhosis, chronic pancreatitis, cholestyramine-induced bile acid loss, cystic fibrosis, lactase deficiency, pancreatic cancer, pancreatic resection, sucrase-isomaltase deficiency, abnormal milieu, abnormal motility secondary to diabetes, scleroderma, hypothyroidism, or hyperthyroidism, bacterial overgrowth due to blind loops (deconjugation of bile salts), diverticula in the small intestine, Zollinger-Ellison syndrome (low duodenal pH), acutely abnormal epithelium, acute intestinal infections, alcohol, neomycin, impaired transport, abetalipoproteinemia, Addison disease, blocked lacteals due to lymphoma or tuberculosis, intrinsic factor deficiency (as in pernicious anemia), lymphangiectasia, jejunoileal bypass for obesity, short bowel syndrome, or other conditions. Other patients may need or want additional dietary supplementation. Further improvements are required to address these and other known issues.

SUMMARY

Exemplary embodiments of the disclosure may be drawn to a device having an inlet and a chamber. Immobilized lipase, immobilized protease, and immobilized amylase may be contained within the chamber. The device may also include an outlet, wherein a flow path extends from the inlet, through the chamber, and to the outlet.

Various embodiments of the device may include one or more of the following features: the chamber may include one or more sections; the lipase, the protease, and the amylase may be contained within one section of the chamber; the chamber may include a first section, a second section, and a third section; the lipase may be contained within the first section, the protease may be contained within the second section, and the amylase may be contained within the third section; the chamber may include a first section and a second section; the first section may contain at least two of the amylase, the protease, or the lipase; the device may further include a supplement, wherein the chamber includes a first section and a second section, and the first section contains the supplement; the supplement may include at least one of a vitamin, a mineral, a nutrient, or a medicament; at least one of the chamber or the one or more sections may be removably coupled to the device; the device may further include a first connector fluidly connected to the inlet and a second connector fluidly connected to the outlet, wherein the first connector and the second connector are dimensioned to connect to a feeding tube; and at least one of the lipase, the protease, or the amylase may be immobilized to a plurality of particles contained within the chamber.

In other exemplary embodiments, a device may include an inlet and a chamber. A lipase, a protease, and an amylase may be contained within the chamber. The device may also include an outlet, wherein a flow path extends from the inlet, through the chamber, and to the outlet so that a nutritional formula flowing through the device is exposed to the lipase, the protease, and the amylase. At least one of the lipase, the protease, and the amylase may be immobilized within the chamber to a solid structure.

Various embodiments of the device may include one or more of the following features: the solid structure may include a plurality of particles contained within the chamber; the device may further include at least one of a vitamin, a mineral, a nutrient, or a medicament; the chamber may include one or more sections, and the lipase, the protease, and the amylase may be contained within the one or more sections; the lipase, the protease, and the amylase may each be contained in separate sections of the one or more sections; at least one of the chamber or the one or more sections may be removably coupled to the device; the lipase, the protease, and the amylase may each be immobilized within the chamber to one or more solid structures; and the device may further include a first connector fluidly connected to the inlet and a second connector fluidly connected to the outlet, wherein the first connector and the second connector are dimensioned to connect to a feeding tube.

Both the foregoing general description and the following detailed description are exemplary and explanatory only and are not restrictive of the features, as claimed. As used herein, the terms "comprises," "comprising," "includes," or other variations thereof, are intended to cover a non-exclusive inclusion such that a process, method, article, or apparatus that comprises a list of elements does not include only those elements, but may include other elements not expressly listed or inherent to such a process, method, article, or apparatus. Additionally, the term "exemplary" is used herein in the sense of "example," rather than "ideal." Further, the terms "first," "second," "third," etc., are used herein for purposes of distinguishing features from one another, rather than denoting order. For example, a first section does not necessarily come before a second section, but rather is used to mean that the first section and the second section are two different features. It should be noted that all numeric values disclosed or claimed herein (including all disclosed values, limits, and ranges) may have a variation of +/−10% (unless a different variation is specified) from the disclosed numeric value. Moreover, in the claims, values, limits, and/or ranges means the value, limit, and/or range+/−10%. Further, although some embodiments are discussed in terms of use for infants, it is contemplated that the methods and devices described herein may be used for subjects of all ages, including the elderly, adults, children, and infants, and for any deficiency, disease, or use not limited to premature birth.

BRIEF DESCRIPTION OF THE DRAWINGS

The accompanying drawings, which are incorporated in and constitute a part of this specification, illustrate the disclosed embodiments, and together with the description, serve to explain the principles of the disclosed embodiments. There are many aspects and embodiments described herein. Those of ordinary skill in the art will readily recognize that the features of a particular aspect or embodiment may be used in conjunction with the features of any or all of the other aspects or embodiments described in this disclosure. In the drawings.

DETAILED DESCRIPTION

Reference will now be made in detail to the exemplary embodiments of the present disclosure described below and illustrated in the accompanying drawings. Wherever possible, the same reference numbers will be used throughout the drawings to refer to same or like parts.

Additional objects and advantages of the embodiments will be set forth in part in the description that follows, and in part will be obvious from the description, or may be learned by practice of the embodiments. It is to be understood that both the foregoing general description and the following detailed description are exemplary and explanatory only and are not restrictive of the claims.

Aspects of the present disclosure are described with reference to devices for supplementing nutritional formulas, and, particularly, to devices for hydrolyzing lipids, proteins, and/or carbohydrates. Although embodiments of the disclosure may generally be described in reference to human milk (e.g., mother's milk or donor milk, either pasteurized or unpasteurized), it will be understood that embodiments of the disclosure may be used to supplement (e.g., with hydrolyzed lipids, proteins, and/or carbohydrates, or vitamins, minerals, and/or nutrients) any nutritional formula or beverage. For example, embodiments of the disclosure may be used with any suitable enteral, infant, or oral formula.

As used herein, the term "nutritional formula" may include complex mixtures containing, for example, proteins, carbohydrates, fats, water, minerals, and/or vitamins. This may include liquid foods that are specially formulated and processed; liquids used for the partial or exclusive feeding of a person by means of oral intake or feeding by tube; liquids used for the dietary management of a person who, because of therapeutic or medical need, has limited or impaired capacity to ingest, digest, absorb, or metabolize ordinary foodstuffs or certain nutrients; liquids that meet medically determined nutrient requirements; and liquids designed to deliver to a subject nutrients that cannot be provided to the subject via dietary management and modification of the normal diet alone. In some examples, "nutritional formula" may include enteral or parenteral formula or may be a mixture of enteral or parenteral formulas.

In some embodiments, nutritional formula may be delivered to the subject under medical supervision, may be intended only for a person receiving active and ongoing medical supervision, or may be delivered to the subject for home use, either when supervised or unsupervised. Nutritional formula may be packaged as a dry powder and then mixed with a solvent to form a solution or may be packaged as a liquid nutritional formula, beverage, or drink. In some embodiments, nutritional formula may be commercially available, or may be prepared by a healthcare professional before feeding. In some embodiments, nutritional formula may include at least one medicament prescribed for the subject in need of the medicament and/or nutritional formula, or nutritional formula may itself be the prescribed medicament. Nutritional formula may be an infant and/or toddler formula as a complete or partial substitute for human milk, may be donor milk, or mother's milk (infant's own mother or other mother's milk), whether pasteurized or unpasteurized.

Nutritional formula may or may not include at least one fat in triglyceride form, such as short-chain triglycerides (SCTs), MCTs, and LCTs. Nutritional formula 110 may or may not include at least one protein and may or may not include at least one carbohydrate. In some embodiments, nutritional formula may further include at least one nutrient selected from water, maltodextrin, proteins, amino acids, peptides, SCTs, MCTs, LCTs, diglycerides, monoglycerides, cornstarch, fish oil, soybean oil, rapeseed oil, cottonseed oil, sunflower oil, olive oil (oils may or may not be refined), soluble fiber, lecithin, magnesium chloride, sodium ascorbate, guar gum, calcium phosphate, salt, choline chloride, phosphoric acid, calcium citrate, sodium phosphate, taurine, magnesium oxide, zinc sulfate, potassium chloride, niacinamide, ferrous sulfate, calcium pantothenate, manganese sulfate, pyridoxine hydrochloride, copper sulfate, thiamine mononitrate, beta-carotene, riboflavin, arginine, palmitate, other antioxidants, folic acid, biotin, selenium (sodium selenite), chromium chloride, potassium iodide, sodium molybdate, soluble fiber, fructooligosaccharide, prebiotic, citric acid, vitamin A, vitamin D, vitamin E, vitamin K, vitamin $B_1$, vitamin $B_2$, vitamin $B_3$, vitamin $B_5$, vitamin $B_6$, vitamin $B_7$, vitamin $B_9$, and vitamin $B_{12}$. Exemplary nutritional formulas and systems are described in U.S. patent application Ser. No. 14/378,856, filed Aug. 14, 2014, now U.S. Pat. No. 9,668,942, which is herein incorporated by reference in its entirety.

In some aspects, exemplary nutritional formulas may include one or more probiotics. As used herein, the term "probiotic" may refer to microorganisms, which, when administered in adequate amounts, may confer a health benefit on the host. The health benefits may include those relating to gut health, oral health, and/or immune health. The probiotics may be prepared in a dry form (e.g., powder). In some examples, the dry form probiotics may be mixed (e.g., dissolved or suspended) with other components in nutritional formulas.

Probiotics described herein may include naturally occurring microorganisms. Alternatively or additionally, probiotics may include modified microorganisms, e.g., microorganisms produced by selective culturing or genetic engineering. Examples of probiotics include, but are not limited to, fungi such as *Saccharomyces, Debaromyces, Candidaw Pichia, Torulopsis, Aspergillus, Rhizopus, Mucor, Penicillium*, and/ or *Torulopsis*, and bacteria such as *Bifidobacterium, Bacteroides, Clostridium, Fusobacterium, Melissococcus, Propionibacterium, Streptococcus, Enterococcus, Lactococcus, Kocuriaw, Staphylococcus, Peptostrepococcus, Bacillus, Pediococcus, Micrococcus, Leuconostoc, Weissella, Aerococcus, Oenococcus*, and/or *Lactobacillus*. In some examples, probiotics in nutritional formulas may include *Aspergillus niger, Aspergillus oryzae, Bacillus coagulans, Bacillus lentus, Bacillus licheniformis, Bacillus mesentericus, Bacillus pumilus, Bacillus subtilis, Bacillus natto, Bacteroides amylophilus, Bacteroides capillosus, Bacteroi-* des ruminocola, Bacteroides suis, Bifidobacterium adolescentis, Bifidobacterium animalis, Bifidobacterium breve, Bifidobacterium bifidum, Bifidobacterium infantis, Bifidobacterium lactis, Bifidobacterium longum, Bifidobacterium pseudolongum, Bifidobacterium thermophilum, Bacillus laterosporus, Bacillus laevolacticus, Candida pintolepesii, Clostridium butyricum, Enterococcus cremoris, Enterococcus diacetylactis, Enterococcus faecium, Enterococcus intermedius, Enterococcus lactis, Enterococcus muntdi, Enterococcus thermophilus, Escherichia coli, Kluyveromyces fragilis, Lactobacillus acidophilus, Lactobacillus alimentarius, Lactobacillus amylovorus, Lactobacillus crispatus, Lactobacillus brevis, Lactobacillus casei, Lactobacillus curvatus, Lactobacillus cellobiosus, Lactobacillus delbrueckii ss. bulgaricus, Lactobacillus farciminis, Lactobacillus fermentum, Lactobacillus gasseri, Lactobacillus helveticus, Lactobacillus lactis, Lactobacillus plantarum, Lactobacillus johnsonii, Lactobacillus reuteri, Lactobacillus rhamnosus, Lactobacillus sakei, Lactobacillus salivarius, Lactobacillus jensenii, Lactobacillus gasserii, Lactobacillus fermentum, Lactobacillus rhamnosus, Lactobacillus salvalarius, Leuconostoc mesenteroides, Pediococcus damnosus, Pediococcus acidilactici, Pediococcus pentosaceus, Pediococcus urinae, Propionibacterium freudenreichii, Propionibacterium shermanii, Saccharomyces cereviseae, Sporolactobacillus inulinus, Staphylococcus carnosus, Staphylococcus xylosus, Streptococcus infantarius, Streptococcus thermophilus, Streptococcus Lactis, any/or derivatives thereof, or any mixtures thereof.

In some aspects, probiotics may be present in nutritional formulas in an amount sufficient to confer a health benefit. In some examples, the concentration of the probiotics in a nutritional formula may range from about $10^2$ colony forming units per gram of nutritional formula (cfu/g) to about $10^{12}$ cfu/g, from about $10^2$ cfu/g to about $10^6$ cfu/g, from about $10^4$ cfu/g to about $10^8$ cfu/g, from about $10^6$ cfu/g to about $10^{10}$ cfu/g, or from about $10^8$ cfu/g to about $10^{12}$ cfu/g. As used herein, the term "about" should be understood to encompass ±5% of a specified amount or value.

In some aspects, exemplary nutritional formulas may additionally, or alternatively include one or more prebiotics. As used herein, the term "prebiotic" includes, but is not limited to, substances that induce the growth and/or activity of the probiotics. Examples of prebiotics include, but are not limited to, non-digestible carbohydrate such as resistant starch, hemicellulose, pectins, gums, galactooligosaccharide, fructooligosaccharide, maltoligosaccharide, lactulose, isomaltose oligosaccharide, transgalactooligosaccharide, xylooligosaccharide, soyoligosaccharide, inulin, arabinogalactan, lactilol, lactosucrose, fiber sources such as oat gum, pea fiber, apple fiber, pectin, guar gum, *psyllium* husks, glucomannan or guar gum hydrolysate, any derivatives thereof, and/or any combinations thereof.

As described above, in some aspects, exemplary nutritional formulas may not contain sufficient amounts of nutrients, e.g., lipids, proteins, and/or carbohydrates, for the needs of a patient, e.g., a premature infant, or a patient may want further supplementation. In some aspects, the nutrients contained in nutritional formulas may not be in a form digestible or absorbable to the patient. Embodiments of the present disclosure may be used to provide a nutritional formula that, as-fed, delivers increased concentrations of hydrolyzed lipids, proteins, and/or carbohydrates, e.g., of monoglycerides, free fatty acids, glucose, and amino acids, which may be absorbed through the gut of an infant or other patient. As a result, formula-fed subjects may be provided with, e.g., one or more of docosahexaenoic acid ("DHA"), eicosapentaenoic acid ("EPA"), arachidonic acid ("ARA" or "AA"), or other lipids, carbohydrates, or proteins that they may not otherwise have had access to or may not have been able to digest.

Embodiments of the present disclosure are drawn to devices and methods for increasing the amount of total calories, energy, proteins, and/or carbohydrates in nutritional formulas and/or increasing the bioavailability of nutrients in nutritional formulas while not significantly increasing the overall volume of nutritional formula fed to the patient (e.g., by increasing the nutrient density of the formula and/or making the nutrients in the nutritional formula easier for the patient to uptake so that a greater portion of the nutrients may be absorbed by the patient). By not substantially increasing the amount of formula to be fed to a patient, or by decreasing the volume of nutritional formula to be fed to a patient due to the increased concentration and/or bioavailability of nutrients, embodiments of the present disclosure may reduce inflammatory responses found in the patient's (e.g., a premature infant's) GI tract and/or may condition the patient's GI tract for improved overall absorption of nutrients, including, but not limited to, protein and vitamins.

According to various embodiments, the present disclosure provides devices and methods for preparing nutritional formulas. The devices and methods may be used to expose infant formula or other nutritional formulas to lipases, proteases, and/or amylases prior to consumption. The lipases will accordingly break down fats and oils with subsequent release of free fatty acids and monoglycerides. The proteases will accordingly break down proteins and peptides with subsequent release of peptides and amino acids. The amylases will accordingly break down carbohydrates, such as sugars and starches, into glucose, simple carbohydrates, and oligosaccharides. The devices and methods will provide a convenient way to prepare nutritional formulas. In some embodiments, the devices and methods allow infants or others who consume the nutritional formulas to avoid consuming exogenous lipase, protease, and/or amylase. In some embodiments, the devices and methods allow for production of formulas that contain monoglycerides, free fatty acids, glucose, and/or amino acids but do not contain any significant amount of lipase, protease, and/or amylase.

Exemplary devices may include one or more chambers containing immobilized or free (i.e., not immobilized) lipase, protease, and/or amylase through which the nutritional formula may be passed in order to hydrolyze the lipids, proteins, and/or carbohydrates in the nutritional formula. Exemplary devices may be fluidly connected to a source of nutritional formula and/or a feeding system for delivering a nutritional formula in order to supplement the nutritional formula with the hydrolyzed lipids, proteins, and/or carbohydrates. Exemplary devices and exemplary systems in which they may be included are described further below.

Figure 1:
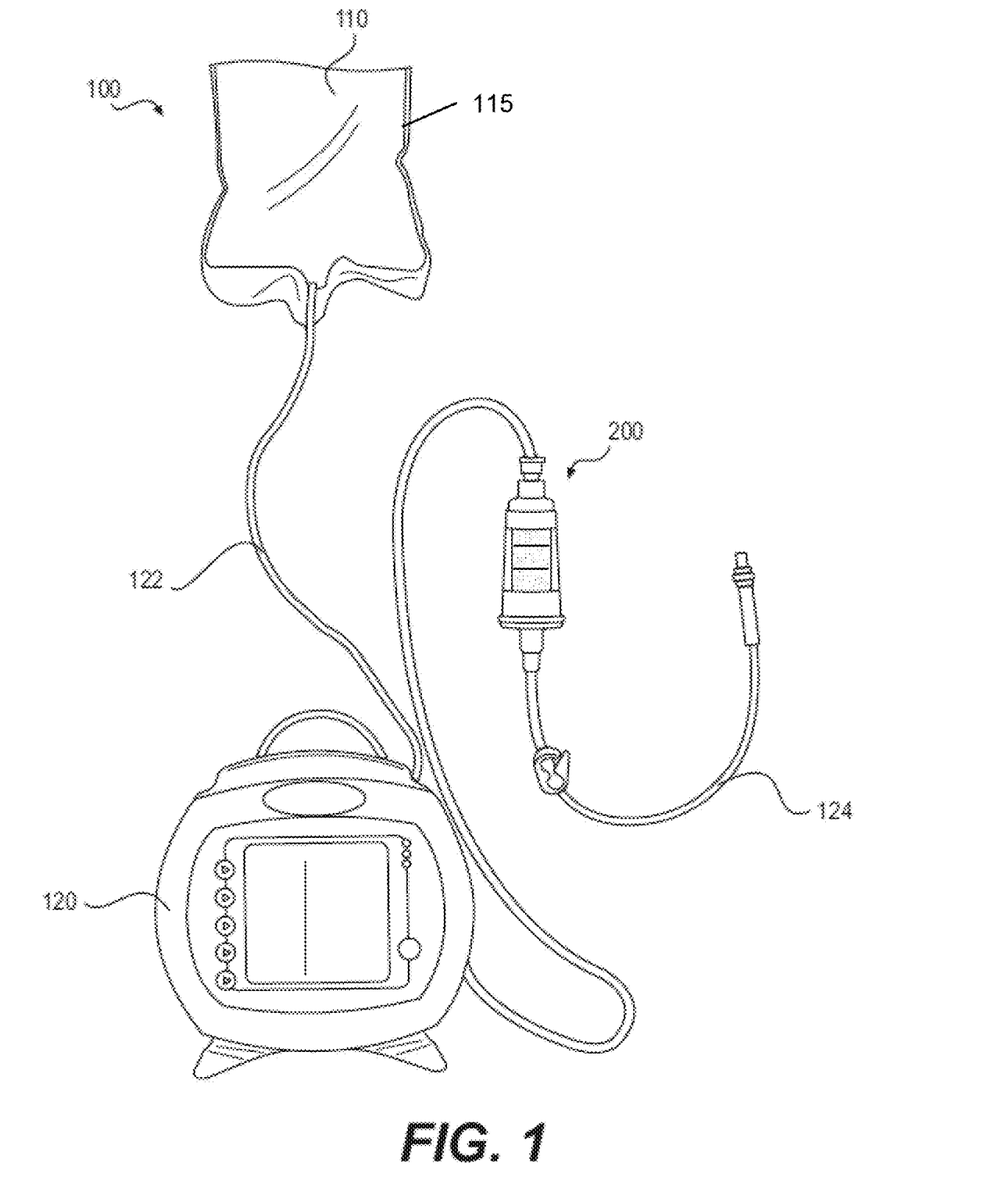
FIG. 1 illustrates an exemplary feeding system, according to embodiments of the present disclosure.

FIG. 1 illustrates an exemplary feeding system 100 for providing a nutritional formula 110 to a subject, e.g., via a feeding tube. In some embodiments, system 100 may be an enteral feeding system, while in other embodiments, system 100 may be a parenteral feeding system. As shown in FIG. 1, devices of the present disclosure may include a container 115 configured to hold nutritional formula 110. An exemplary system 100 may include a pump 120 and a tube 122 fluidly connecting a source of nutritional formula 110 to an outlet configured to output nutritional formula 110 to a patient for ingestion. Container 115 may include, e.g., a feeding bag, a vial, a syringe, a bottle, or any other suitable container. Nutritional formula 110 may be flowed from the source container, through tube 122, and to the patient. Tube 122 may be an enteral feeding tube, for example, a gastric, a nasogastric, a nasoduodenal, a nasojejunal, a gastrostomy, a gastrojejunostomy, a jejunostomy, a percutaneous endoscopic gastrostomy (PEG) tube, or a transjejunal feeding tube to feed nutritional formula 110 to the GI tract of a subject through, for example, the nose, mouth, stomach, or abdomen of the patient. In such embodiments, system 100 may be used in line with standard enteral feeding practice. In some embodiments, tube 122 may be a parenteral feeding tube to feed nutritional formula 110 to the bloodstream of a subject through, for example, the external or internal jugular veins, the subclavian and axillary veins, the femoral vein, veins in the arms, veins in the legs, or veins in the scalp. In such embodiments, system 100 may be used in line with standard parenteral feeding processes.

The flow of nutritional formula 110 through system 100 of FIG. 1 may be controlled by pump 120 of system 100. In some embodiments, pump 120 may be a peristaltic pump, although any suitable type of infusion pump, e.g., an elastomeric pump, a multi-channel pump, a syringe pump, and/or a smart pump may be used. A flow rate of nutritional formula 110 through the tubes and/or device 200 may be set and/or adjusted by pump 120. In some embodiments, pump 120 may include a processor, a display, and/or actuators (e.g. buttons, knobs, touch screen, etc.) to adjust and control the flow rate of nutritional formula 110 in system 100 and device 200. Pump 120 may be adjusted and set by a healthcare provider and/or the subject receiving nutritional formula 110. Pump 120 may perform continuous feeding, pulsatile feeding, intermittent feeding, bolus feeding, and/or flushing, and delivery of fluids may be set or adjusted automatically, semi-automatically, or manually.

In other embodiments, system 100 of FIG. 1 may not include pump 120 and may instead depend on gravity to flow nutritional formula 110 from container 115 to the subject. The relative positioning of the source of nutritional formula 110 may allow nutritional formula 110 to flow through the tubes and device 200 under the influence of gravity alone. For example, container 115 of nutritional formula 110 may be placed above the attached tubing, above device 200, and/or above the patient.

In other embodiments, pump 120 of system 100 may be replaced with a syringe. The syringe may be filled with nutritional formula 110, and the flow rate of nutritional formula 110 in the tubes and device 200 may be set, and/or adjusted by using the syringe manually, semi-automatically, or automatically. For example, nutritional formula 110 may be pre-packaged in a pre-filled syringe mounted inside of an auto-injector-like device. The pre-packaged formula may also contain a pump 'engine' (e.g., a spring-loaded piston), and may be used to deliver the formula through system 100 and to the subject, or may be used in any other feeding system.

In other embodiments, system 100 may use any suitable means, e.g., a balloon or other suitable pressure-generating device, to generate a pressure drop or a flow-driving force that drives nutritional formula 110 through the tubes and/or device 200.

System 100 of FIG. 1 may include a fat, protein, and/or carbohydrate hydrolysis device 200. Nutritional formula 110 may be flowed from the container 115, through first tube 122, and to device 200, where nutritional formula 110 is hydrolyzed. System 100 may also include a second tube 124 having a first end configured to connect to an outlet of device 200 and a second end, opposite the first end, configured to connect to a patient-delivery device (e.g., a port, catheter, needle), or directly to a patient, to deliver processed nutritional formula 110 from device 200 to the patient for administration. Second tube 124 may be an enteral feeding tube, for example, a gastric, a nasogastric, a nasoduodenal, a nasojejunal, a gastrostomy, a gastrojejunostomy, a jejunostomy, a percutaneous endoscopic gastrostomy (PEG) tube, or a transjejunal feeding tube to feed nutritional formula 110 to the GI tract of a subject through, for example, the nose, mouth, stomach, or abdomen of the patient. System 100 may be used in line with standard enteral feeding practice. In some embodiments, tube 124 may be a parenteral feeding tube to feed nutritional formula 110 to the bloodstream of a subject through, for example, the external or internal jugular veins, the subclavian and axillary veins, the femoral vein, veins in the arms, veins in the legs, or veins in the scalp. In such embodiments, system 100 may be used in line with standard parenteral feeding processes. Exemplary embodiments of feeding system 100 and hydrolysis device 200 are described in U.S. patent application Ser. No. 15/291,530, filed Oct. 12, 2016, and U.S. patent application Ser. No. 14/378,856, filed Aug. 14, 2014, now U.S. Pat. No. 9,668, 942, both of which are herein incorporated by reference in their entireties.

System 100 of FIG. 1 is configured to deliver and process nutritional formula 110, e.g., at the point of care, so that device 200 may hydrolyze fats, proteins, and/or carbohydrates contained in nutritional formula 110 prior to administration of the nutritional formula to a subject. As used herein, "processing" by device 200, or any other device discussed herein, may refer to hydrolyzing fats, proteins, and/or carbohydrates already contained within nutritional formula 110 by exposing nutritional formula 110 to lipases, proteases, and/or amylases contained within device 200. Processing may also refer to supplementing nutritional formula 110 with additional nutrients that may be contained within device 200. As described in detail below, device 200 may include one or more lipases, proteases, and/or amylases.

In some embodiments, one or more of the lipases, proteases, and/or amylases may be immobilized such that nutritional formula 110 that is fed to the subject via an enteral or parenteral feeding mechanism, or other feeding mechanism (e.g., a baby bottle), does not contain one or more of the lipases, proteases, and/or amylases in any appreciable amount. For example, the lipases, proteases, and/or amylases may be immobilized on or in structures of device 200 found along the wall or otherwise within the container such that the lipases, proteases, and/or amylases are in fluid contact with nutritional formula 110 being passed through device 200. Further, as is discussed with reference to various embodiments below, nutritional formula 110 may be added to device 200 in various ways to allow enzymatic treatment of lipases, proteases, and/or amylases within device 200. System 100 of FIG. 1 is provided only as an example of a feeding system with which device 200 may be used. The present disclosure is drawn to devices and methods for supplementing nutritional products and may be used in conjunction with any other suitable feeding system.

The devices and methods disclosed herein may be used to expose a nutritional formula 110 to lipases, amylases, and/or proteases to hydrolyze lipids, proteins, and/or carbohydrates in the nutritional formula 110 prior to consumption. In some embodiments, the devices and methods provide formulas that contain monoglycerides, free fatty acids, amino acids, and/or glucose or an increased concentration of monoglycerides, free fatty acids, amino acids, and/or glucose, but do not contain a significant amount of lipase, protease, and/or amylase, or contain no lipase, protease, and/or amylase.

Figure 2A:
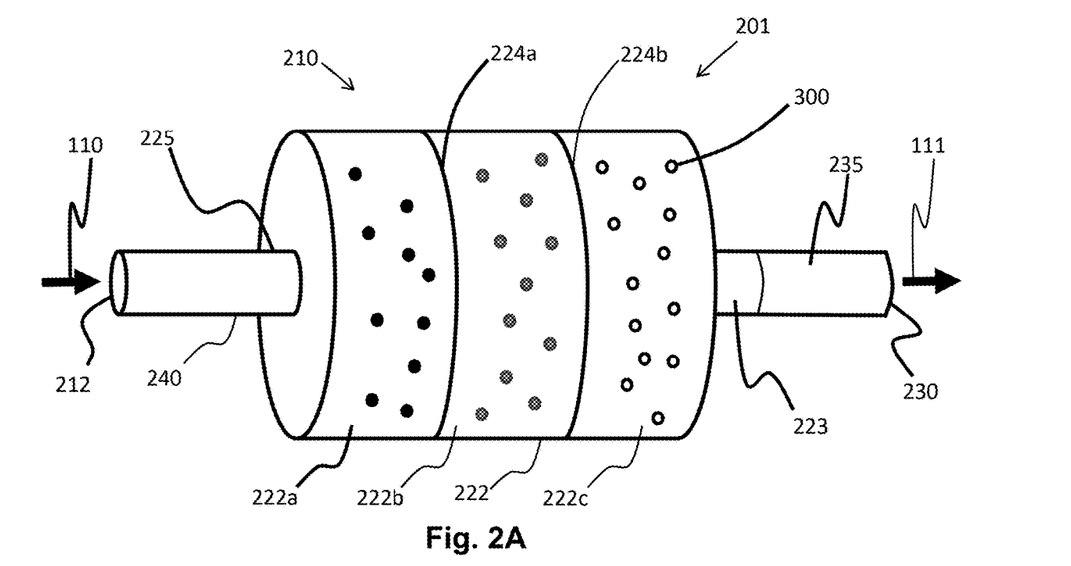
FIG. 2A illustrates an exemplary device for processing a nutritional formula, according to embodiments of the present disclosure.

FIG. 2A illustrates an exemplary device 201 in accordance with embodiments of the present disclosure. Device 201 may include a body 210 having an inlet 212, a chamber 222, and an outlet 230. Chamber 222 may include three separate sections 222a, 222b, 222c. Sections 222a, 222b, 222c may be spaced apart from one another in chamber 222, may directly abut each other in chamber 222, or may be formed via partitions dividing portions of chamber 222. Each section may be uniform in shape and/or size, or one or more sections may vary in shape and/or size. While FIG. 1 depicts three sections in chamber 222, in various embodiments, chamber 222 may include a single section, two sections, or four or more sections. One or more of sections 222a, 222b, 222c may be fixed within chamber 222 and/or body 210 or may be removable from chamber 222 and/or body 210 of device 201. Chamber 222 may be removable or fixed within body 210. Although a chamber 222 containing sections is described, it is contemplated that body 210 may contain each of the sections and a separate chamber 222 may not be included.

Each section 222a, 222b, 222c may contain an enzyme. For example, each section may contain a different enzyme or a different combination of enzymes, or some sections may contain the same type of enzymes as another section. In some embodiments, sections 222a, 222b, 222c may contain one of lipase, amylase, or protease. The sections may contain a single type of enzyme (e.g., all lipases, all amylases, or all proteases), may contain a single type of lipase, amylase, or protease, or may contain a combination thereof (e.g., multiple types of lipases, multiple types of amylases, or multiple types of proteases). The sections may be arranged in any order so that any of the amylase section, the protease section, or the lipase section may be located furthest upstream, furthest downstream, or in the middle of chamber 222. Enzymes in the various sections may be free (i.e., not immobilized) or immobilized, or a combination thereof. For example, one or more sections may contain one or more structures (e.g., one or more walls of the sections or separate structures, for example, a plurality of particles 300) to which lipase, protease, and/or amylase may be immobilized, e.g., via covalent or ionic binding or by absorption, for example.

The enzymes contained in the various sections may react with nutritional formula as nutritional formula flows from inlet 212 to outlet 230 through chamber 222. For example, lipase in one section may hydrolyze lipids present in the nutritional formula as the nutritional formula flows through the lipase section, protease in one section may hydrolyze proteins present in the nutritional formula as the nutritional formula flows through the protease section, and amylase in one section may hydrolyze carbohydrates present in the nutritional formula as the nutritional formula flows through the amylase section.

As shown in FIG. 2A, sections 222a, 222b, 222c may be separated by section interfaces 224a, 224b, which may include one or more filters. Section interfaces 224a, 224b may allow nutritional formula containing one or more of hydrolyzed lipids, hydrolyzed proteins, and/or hydrolyzed carbohydrates to pass through, for example from section 222a to section 222b, or from section 222b to section 222c, and may not allow lipases, proteases, and/or amylases (and/or structures to which they are bound) to pass through each section interface 224a, 224b. In some aspects, interfaces 224a, 224b, may allow some enzymes, such as lipase, protease, or amylase, to pass through but may prevent other specific enzymes from flowing through the interface. Interfaces 224a, 224b may be filters and/or may be made of any suitable material and may have any suitable coating.

In some embodiments, sections 222a, 222b, 222c may be separated by one or more valves to control the flow of nutritional formula. In some embodiments, one or more sections may include an outlet and/or an inlet through which nutritional formula exits or enters the section. The outlet and/or inlet may have a width that is less than the width of chamber 222 or the maximum width of the individual section, or the outlet and/or inlet may have a width that is equal to the width of chamber 222 or the maximum width of the individual section. In some embodiments, the outlet of one section may be fluidly connected to the inlet of the adjacent section. In some embodiments, the inlets and outlets of the different sections may directly connect, or they may be spaced apart. If they are spaced apart, tubing, a funnel, or some other suitable structure may connect the section outlets and inlets.

Separate sections 222a, 222b, 222c may include one of lipase, amylase, and/or protease, and the lipase, amylase, and/or protease may or may not be immobilized. In some examples, section 222a may include immobilized lipase, section 222b may include immobilized protease, and section 222c may include immobilized amylase. In other examples, chamber 222 may include two sections. Each of the two sections may contain one of lipase, protease, or amylase. In other embodiments, one or both of the two sections may contain two enzymes (e.g., lipase and protease, lipase and amylase, protease and amylase) and/or one of the sections may contain lipase, protease, and/or or amylase. In other examples, chamber 222 may include more than three sections, with lipase, protease, and/or amylase (or any combination thereof) contained within any number of the more than three sections of chamber 222. Separate sections 222a, 222b, 222c may be part of a single chamber 222 or may each be separate chambers arranged in series within chamber 222 and/or body 210. The separate sections or chambers may be interchangeable, replaceable, and/or refillable, or may be fixed within chamber 222 and/or body 210. In some embodiments, chamber 222 may be removable from body 210, or each section may be removable from chamber 222 and/or body 210. In some embodiments, one or more of body 210, chamber 222, and/or sections 222a, 222b, 222c may be sterilized or sterilizable. In some embodiments, one or more of chamber 222 and/or sections 222a, 222b, 222c may be pre-filled with particles and/or enzymes (e.g., protease, amylase, and/or lipase.

In some embodiments, one or more of chamber 222 and/or sections 222a, 222b, 222c may be provided in a closed, sealed configuration and may be opened shortly prior to installation within device 201. In some embodiments, a user (e.g., healthcare provider, patient, patient guardian, pharmacist, or other user) may insert and/or install one or more of chamber 222 and/or sections 222a, 222b, 222c into device 201 prior to use. In some embodiments, one or more of chamber 222 and/or sections 222a, 222b, 222c may be pre-filled. In other embodiments, a user may fill one or more of chamber 222 and/or sections 222a, 222b, 222c with the desired type and/or amount of enzyme (whether or not bound to structures, e.g., particles) or combination thereof. In some embodiments, one or more of chamber 222 and/or sections 222a, 222b, 222c may be removable and disposable after use, and/or configured to be cleaned, sterilized, and refilled such that it may be reused. In other embodiments, one or more of chamber 222 and/or sections 222a, 222b, 222c may be permanently housed within device 210. In some examples, one or more of chamber 222 and/or sections 222a, 222b, 222c may include an access port for refilling the section or emptying the section of its contents.

Device 201 may also include an interface 225 through which nutritional formula containing un-hydrolyzed lipids, proteins, and/or carbohydrates may flow into device 201 from a source of nutritional formula. In some embodiments, interface 225 may be configured to fluidly connect to a connector 240, or to fluidly connect to a feeding tube (e.g., an enteral or parenteral feeding tube), tubing from a breast pump, or a connection from another source of nutritional formula. In some embodiments, device 201 may not include an interface 225 and may directly connect to tubing or other devices connected to a source of nutritional formula or may connect directly to a source of nutritional formula.

Device 201 may also include an interface 223 through which nutritional formula containing hydrolyzed lipids, proteins, and/or carbohydrates may pass out of device 210 to be fed to a subject. In some embodiments, interface 223 may be configured to fluidly connect to a connector 235, or to a feeding tube (e.g., an enteral or parenteral feeding tube) or to an opening in any other suitable container in which nutritional formula may be stored or administered (e.g., a bottle, cup, bag, vial, etc.). In some embodiments, device 201 may not include an interface 223 and may directly connect to, e.g., tubing, a feeding device, or a patient.

In the embodiment of FIG. 2A, interfaces 223, 225 are fluidly connected to connectors 235, 240, respectively. Connectors 235, 240 may be part of device 201 or may be separate from device 201 and configured to removably connect to device 201 (e.g., via interface 223, 225). In some embodiments, device 201 may not include connectors 235, 240. Connector 240 may be configured to fluidly couple to a source of nutritional formula 110 and to receive an input of nutritional formula 110. For example, connector 240 may be configured to fluidly connect to a feeding tube (e.g., an enteral or parenteral feeding tube), tubing from a breast pump, or a connection from another source of nutritional formula. Connector 235 may be configured to fluidly couple to a structure, e.g., a feeding tube, configured to deliver processed nutritional formula 111 to a subject and may be configured to discharge an output of processed nutritional formula 111. For example, connector 235 may be configured to fluidly connect to a feeding tube (e.g., an enteral or parenteral feeding tube) or to an opening in any other suitable container in which nutritional formula 110 may be stored or administered (e.g., a bottle, cup, bag, vial, etc.).

In some embodiments, first connector 240 and/or second connector 235 may be configured to fluidly connect to one or both of first tube 122 and enteral or parenteral tube 124 of system 100 (FIG. 1), for example, where device 200 is located. As nutritional formula 110 flows through system 100 (or any other suitable feeding system), nutritional formula 110 from a source may be received within connector 240 and may flow through interface 225, chamber 222, one or more of sections 222a, 222b, and 222c (or additional sections, depending on which sections are included in device 201), and may flow though interface 223 out of connector 235. While in chamber 222, lipase, protease, and/or amylase in one or more of the sections may hydrolyze lipids, proteins, and/or carbohydrates in nutritional formula 110, and then processed nutritional formula 111 may flow through interface 223 and out of connector 235 for administration to a subject. Device 201 may be configured so that lipase, protease, and/or amylase remains within chamber 222, and/or within its respective section, while nutritional formula 110 is allowed to pass through device 201 and processed nutritional formula 111 exits device 201 to be fed to a subject.

Connector 240 and connector 235 may include, e.g., a luer-lock connection, threads, projections, grooves, deformable or expandable structures, and/or any other suitable mechanism for connecting to one or more tubes or devices for carrying nutritional formula from a source and/or to a patient. One suitable connector known in the art is the ENFit® connector (GEDSA). In some embodiments, connector 240 and/or connector 235 may be configured to engage a baby bottle, baby bottle nipple, or any other structure to facilitate transfer of fluid to another container and/or to assist in feeding or storing. Further, one or both of connector 240 and connector 235 may include a valve or other fluid flow control mechanism or a filter.

Interfaces 223, 225 may, in some embodiments, include one or more filters and may prevent particles 300 (or other structures to which lipase, protease, and/or amylase may be immobilized) from exiting chamber 222 of device 201. Additionally or alternatively, the filters in device 201 (such as interfaces 223, 225, 224a, 224b) may prevent foreign objects from entering chamber 222 and/or feeding tube 124. One or more of interfaces 223, 225, 224a, 224b may include semi-permeable membranes that prevent or inhibit enzymes (lipase, protease, and/or amylase) from leaking between sections of chamber 222, out of device 201, and/or into processed nutritional formula 111 exiting device 201. Particles 300 (or other structures on which lipase, protease, and/or amylase may be immobilized) may be separated by interface 225 and interface 223 (in embodiments in which interfaces or filters are used between sections). Interfaces 225, 223 may retain particles 300 (or other structures and/or enzymes) within chamber 222 and/or within their own sections as nutritional formula 110 flows through device 201.

In one exemplary embodiment, chamber 222 of device 201 may be made of a clear plastic or glass so that the plurality of particles 300 inside chamber 222 (or other structures or enzymes) are visible to the user. In some instances, this may allow the user to ensure proper flow through device 201, for example, by visual inspection. In other embodiments, chamber 222 may be opaque or may be made of any suitable material. Particles 300 contained in device 201 may have lipase, protease, and/or amylase immobilized on their surfaces, and as nutritional formula 110 flows through chamber 222 and particles 300, the immobilized lipase, protease, and/or amylase hydrolyzes the fats (e.g., triglycerides), proteins, and/or carbohydrates within nutritional formula 110.

In some embodiments, chamber 222 may be filled/refilled with immobilized lipases, proteases, and/or amylases or may come pre-filled and may not be refillable, as described above. In some such embodiments, a user may select between devices 201 prefilled with different enzymes (e.g., lipase, protease, amylase), combinations of enzymes, and/or volumes of enzymes prior to use. Chamber 222 may be replaceable, and device 201 may be able to separate into its constituent parts to interchange chamber 222, one or more sections, or any other component of device 201. A refillable chamber 222 and/or refillable sections may be refillable prior to, during, and/or after use. If chamber 222 and/or the sections are refillable, they may have one or more inlets (not shown), e.g., one or more re-sealable inlets. In some embodiments, a user (e.g., healthcare provider, patient, patient guardian, pharmacist, or other user) may assembly device 201 prior to use. For example, the user may select a pre-filled chamber 222 and/or desired individual sections containing the desired enzymes and may assemble device 201 with the selected, pre-filled chamber 222 and/or pre-filled sections. In some embodiments, chamber 222 and/or the individual sections may be pre-filled, and a user may select between different types of enzymes or combinations of enzymes and/or may select between different volumes of enzymes, depending, e.g., on the needs of the patient. In such embodiments, chamber 222 and/or the sections may have a sealed opening that is either unsealed prior to assembly of device 201, or the action of assembling chamber 222 and/or the sections within device 201 may break the seal(s) (e.g., perforate, puncture, displace, or otherwise open the seal). A user may fill chamber 222 and/or the sections with the desired type of enzymes, combination of enzymes, and/or desired volume of enzymes prior to and/or during use. In some examples, device 201 may be reusable, and in other examples device 201 may be disposable.

In some embodiments, a valve, frit, mesh, filter, or other mechanical structure may be used to maintain enzymes in chamber 222 and/or the individual sections prior to use and/or to control the flow of nutritional formula 110 through chamber 222 during use. A valve may be included in any one of connectors 240, 235, inlet 212, outlet 230, between sections 222a, 222b, 222c, and/or at interfaces 225, 223, 224a, 224b.

In some embodiments, enzymes (e.g. lipase, protease, and/or amylase) may be mixed, heated, cooled, agitated, or otherwise prepared before and/or during use. For example, device 201 may include a vibrator to agitate device 201 and chamber 222 to mix and/or agitate the enzymes and/or nutritional formula 110. In some embodiments, a vibrating motor may be included in or attached to device 201 to vibrate device 201, agitate enzymes contained within sections of chamber 222, nutritional formula 110, and/or chamber 222, promote mixing of enzymes (lipase, protease, and/or amylase) with nutritional formula 110, assist the flow of nutritional formula 110 through chamber 222, and/or to assist the flow of processed nutritional formula 111 out of outlet 230.

Nutritional formula 110 may flow through device 201 in any suitable manner. In some embodiments, nutritional formula 110 may be gravity-fed through device 201, where nutritional formula 110 is processed (e.g., lipids, proteins, and/or carbohydrates are hydrolyzed), and then processed nutritional formula 111 may flow out of device 201 and may be fed to a subject or stored, e.g., in bulk. In some embodiments, fluidly connecting device 201 to a feeding system (for example systems 100 of FIG. 1) may promote the flow of nutritional formula through device 201, including chamber 222. For example, the flow of nutritional formula 110 out of device 201 may be driven by a pump or other suitable mechanism, as described above.

Figure 2B:
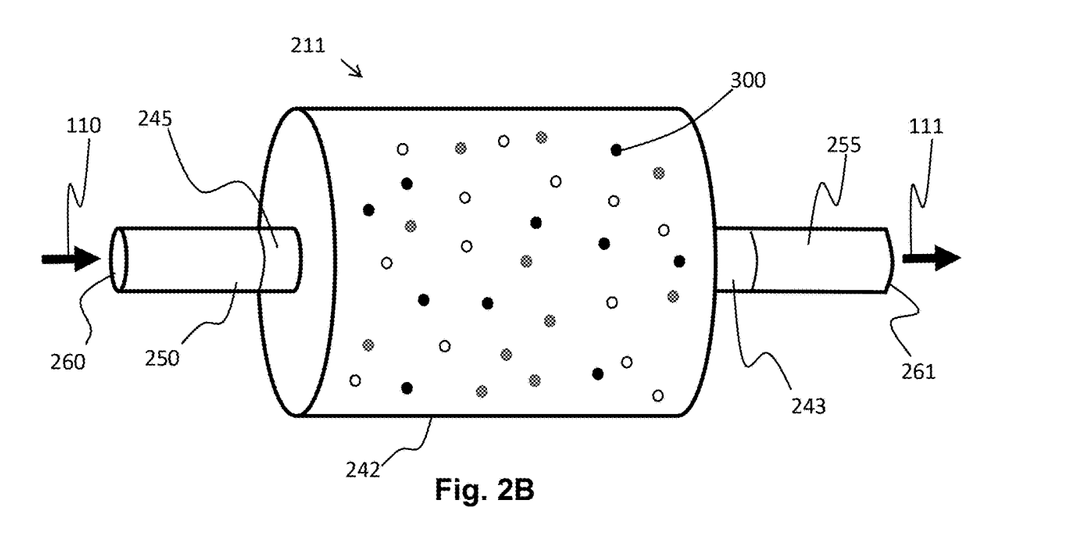
FIG. 2B illustrates an exemplary device for processing a nutritional formula, according to embodiments of the present disclosure.

FIG. 2B shows another exemplary embodiment of a device for processing nutritional formula. Device 211 may be substantially the same as device 201, except without any sections separating different compartments of chamber 242. Device 211 may include, similar to device 201, an inlet 260, an outlet 261, connectors 250, 255, interfaces 245, 243, and particles 300 (or other structures), which may have any of the previously described features and configurations as described in relation to device 201. Lipase, protease, and/or amylase may be present within chamber 242 and may be intermixed throughout chamber 242. In some examples, more than one enzyme (lipase, protease, amylase) may be immobilized on one or more solid supports, e.g., particles 300, membranes, fibers, or other structures, may be immobilized on any surface of chamber 242 or interfaces 245, 243, or may be present within chamber 242 without being immobilized. Each enzyme may be immobilized on its own structure or structures within chamber 242, or multiple enzymes may be immobilized on the same structure or structures within chamber 242, or a combination thereof. In some embodiments, one or more dry enzymes may not interact with each other when stored within chamber 242 but may interact with nutritional formula as the enzymes are wetted when the nutritional formula flows through. In some embodiments, one or more dry enzymes may be coated (e.g., with enteric coating polymers) so that they do not interact with each other when stored within chamber 242 but interact with nutritional formula as the enzymes are wetted when the nutritional formula flows through.

As shown in FIGS. 2A and 2B, in some embodiments, particles 300 may be formed as substantially spherical beads. In other embodiments, particles 300 may be randomly shaped or irregular particles, or may be elliptical, oblong, donut-shaped, a prism, polygonal, elongated, or any other suitable shape or shapes. Particles 300 may have a smooth or a textured surface. Particles 300 may be shaped to increase or decrease their surface area. Particles 300 may be formed of individual particles, which may each have substantially the same shape and/or surface or may have two or more different shape and/or surface combinations. Particles 300 may be formed of any suitable material, and lipase, protease, and/or amylase may be immobilized on particles 300 in any suitable manner, e.g., via adsorption, ionic binding, covalent binding, cross-linking, encapsulation, and/or entrapment. Lipases, proteases and/or amylases may be immobilized on or in particles 300 found within the chamber 222 such that the lipases, proteases and/or amylases are in fluid contact with nutritional formula 110 as nutritional formula 110 flows through chamber 222 and/or individual sections.

While particles 300 are depicted in the exemplary figures, it is appreciated that lipase, protease, and/or amylase may be immobilized in chamber 222 in any suitable manner. For example, lipases, proteases, and/or amylases may be immobilized or contained within structures located inside chamber 222, such as beads, rods, projections extending from portions of chamber 222, or other suitable structures. In some embodiments, lipases, proteases, and/or amylases may be immobilized on or contained within a wall of chamber 222, and/or may be immobilized on one or more filters included in device 200, device 201, and/or device 211. Lipase, protease, and/or amylase may be immobilized on or within a component of any one of devices 200, 201, or 211 so that as nutritional formula 110 flows into the device, such as inside chamber 222 or individual sections, the nutritional formula 110 comes into contact with the lipase, protease, and/or amylase to produce the desired enzymatic effects.

It is also contemplated that, in some embodiments, lipase, protease, and/or amylase may not be immobilized and may simply be contained within chamber 222 or within a section of chamber 222. In some such embodiments, one or more filters may keep the free (i.e., not immobilized) lipase, protease, and/or amylase within chamber 222 and/or device 201. In other examples, one or more of lipase, protease, and/or amylase may be allowed to exit chamber 222 and/or device 201 to enter into nutritional formula 110.

As nutritional formula 110 flows into device 201 and chamber 222, nutritional formula 110 comes into contact with the lipase, protease, and/or amylase contained within chamber 222, and the lipids, proteins, and/or carbohydrates in the nutritional formula are hydrolyzed. The lipase, protease, and/or amylase (immobilized or free) may be located along the flow path of nutritional formula 110 as it flows through chamber 222. After nutritional formula 110 comes into contact with the lipase, protease, and/or amylase, processed nutritional formula 111 may be fed to a subject or stored.

Lipase included in the devices herein may cleave two out of three bonds in a triglyceride, i.e., at the sn-1 and sn-3 positions, leaving an sn-2 monoglyceride. Exemplary lipases may be obtained from animals, plants, natural or genetically engineered microorganisms, or a combination thereof. In some embodiments, the lipase may include one or more of, e.g., a *Chromobacterium viscosum, Pseudomonas fluorescens, Burcholderia cepacia,* or *Rhizopus oryzae* lipase, or any other suitable wild-type or recombinant lipase or combination thereof. In some embodiments, lipase may include phospholipase, e.g., phospholipase A, B, C, D, lecithinase, or any other suitable wild-type or recombinant lipase or combination thereof. Recombinant lipase may have the same or different amino acid sequences than wild-type occurring lipase.

Exemplary proteases that may be included in the devices herein may include one or more of serine, cysteine, threonine, aspartic, glutamic, asparagine, and metalloproteases, pepsin, chymotrypsin, trypsin, or any other suitable wild-type or recombinant lipase or combination thereof. Recombinant protease may have the same or different amino acid sequences than wild-type occurring protease. Suitable proteases may be derived from, e.g., bacterial, fungal, yeast, insect, and/or mammalian sources.

Exemplary amylases that may be included in the devices herein may include one or more of α-amylase (calcium metalloenzymes); β-amylase, γ-amylase, or any other suitable wild-type or recombinant lipase or combination thereof. Recombinant amylases may have the same or different amino acid sequences than wild-type occurring amylase. Suitable amylases may be derived from, e.g., bacterial, fungal, yeast, insect, and/or mammalian sources.

It is also contemplated that devices 200, 201, 211 may include one or more separate sections and/or chambers that contain one or more nutrients, vitamins, minerals, and/or medicaments to supplement nutritional formula 110. The section(s) or chamber(s) may be located upstream, downstream, or interspersed within the section(s) or chamber(s) containing enzymes. As nutritional formula 110 passes through the one or more sections or chambers containing the supplement, the supplement may be added to the nutritional formula.

In some embodiments, the one or more sections or chambers may contain a fat, protein, and or carbohydrate for addition to nutritional formula 110. In such embodiments, the supplemental chamber or section may be located upstream of a chamber and/or section containing the enzyme (e.g., lipase, protease, and/or amylase) that hydrolyzes the supplemental nutrient. For example, a chamber or section containing one or more omega-3 fatty acids may be located upstream of a chamber or section containing lipase, such that nutritional formula is first supplemented with the omega-3 fatty acid, which is then broken down by the lipase within the device. In another example, a supplemental chamber or section containing one or more sources of protein may be located upstream of a chamber or section containing protease, such that nutritional formula is first supplemented with the protein(s), which is then broken down by the protease within the device.

In some embodiments, a chamber or section containing one or more medicaments, such as an antacid, proton pump inhibitor, an antiemetic or other medicament may be located upstream or downstream of one or more enzyme chambers or sections, such that nutritional formula is supplemented with the medicament, which is then delivered to the GI track.

Figure 2C:
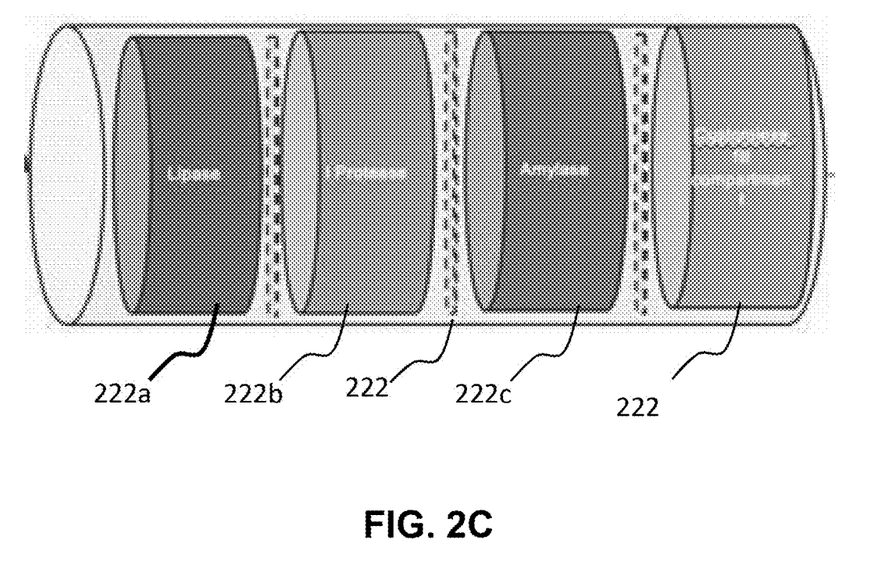
FIG. 2C illustrates an exemplary device for processing a nutritional formula, according to embodiments of the present disclosure.

FIG. 2C schematically depicts an exemplary chamber 222 of a device having a plurality of sections 222a, 222b, 222c, and 222d. Sections 222a, 222b, 222c may include one or more enzymes, for example, lipase, protease, and/or amylase. Chamber 222 may also include a section 222d containing a supplement to be added to nutritional formula, as discussed above. For example, section 222d may contain a nutrient, vitamin, mineral, and/or medicament. In some embodiments, section 222d may include one or more enzymes that may assist with the absorption, utilization, storage, and/or excretion of components found in the nutrition formula. For example, enzymes that aid in the bioconversion of free fatty acids into phospholipids may be included in section 222d. Phospholipids are more readily incorporated into the cellular membrane structures of mammalian cells of various tissues and blood components. Exemplary enzymes that may convert free fatty acids into phospholipids, and that may be incorporated into section 222d, are included in the chart below.

| Enzymes (Symbol and Name) | Lipids (Symbol and Name) |
|---|---|
| AGPAT, 1-acyl-sn-glycerol-3-phosphate O-acyltransferase | AcylGnP, 1-acyl-glyceronephosphate |
| AGNPR, acyl/alkylglycerone-phosphate reducatase | AlkylGnP, 1-alkyl-glyceronephosphate |
| AGNPS, alkylglycerone-phosphate synthase | AlkylGP, 1-alkyl-glycerophosphate |
| CDS, phosphatidate cytidylyltransferase | CDP-DG, CDP-diacylglycerol |
| CEPT, diacylglycerol choline/ethanolaminephosphotransferase | Cer, N-acylsphingosine (ceramide) |
| CERT, ceramide transfer protein | CerPCho, ceramide phosphocholine (sphingomyelin) |
| CGT, N-acylsphingosine galactosyltransferase | CL, diacylglycerophosphoglycerophosphodiradylglycerol |
| CPT, diacylglycerol cholinephosphotransferase | DG, diacylglycerol |
| CLS, cardiolipin synthase | dhCer, dihydroceramide |
| CRD, ceramidase | GalCer, galactosylceramide |
| DGAT, ciacylglycerol O-acyltransferase | GlcCer, glucosylceramide |
| DHCD, dihydroceramide δ (4)-desaturase | DGP, diacylglycerophosphate |
| EPT, ethanolaminephosphostransferase | DGPCho, diacylglycerophosphocholine |
| GCS, ceramide glucosyltransferase | DGPEtn, diacylglycerophosphoethanolamine |
| GNPAT, glycerone-phosphate O-acyltransferase | DGPGro, diacylglycerophosphoglycerol |
| GPAT, glycerol-3-phosphate O-acyltransferase | DGPGroP, diacylglycerophosphoglycerophosphate |
| KDSR, 3-ketosphinganine reductase | DGPIns, diacylglycerophosphoinositol |
| LCS, polypeptide N-acetylgalactosaminyltransferase | GPSer, diacylglycerophosphoserine |
| PAP, phosphatidic acid phosphatase | kSphn, 3-ketosphinganine |
| PED, plasmanylethanolamine desaturase | LacCer, lactosylceramide |
| PEMT, phosphatidylethanolamine N-methyltransferase | MGP, monoacylglycerophosphate |

-continued

| Enzymes (Symbol and Name) | Lipids (Symbol and Name) |
|---|---|
| PGP, phosphatidylglycerophosphatase | PlmaH, 1-alkyl,2-acylglycerol |
| PGS, CDP-diacylglycerol-glycerol-3-phosphate 3-phosphatidyltransferase | PlmaP, 1-alkyl,2-acyl-glycerophosphate |
| PIS, CDP-diacylglycerol-inositol 3-phosphatidyltransferase | PlmaPEtn, 1-alkyl,2-acylglycerophosphophoethanoalmine (plasmanylethanolamine) |
| PSD, phostatidylserine decarboxylase | PlmePCho, 1 Z-Alkenyl-2-acyl-glycerophosphocholine (plasmenylcholine) |
| PSS1, phosphatidylserine synthase 1 | PlmePEtn, 1 Z-Alkenyl,2-acylglycerophosphoethanolamine (plasmenylethanolamine) |
| PSS2, phosphatidylserine synthase 2 | |
| SGMS, ceramide cholinephosphotransferase | |
| SNAT, sphingosine N-acyltransferase | |
| SPK, sphinganine kinase | Sph, sphingosine |
| SPP, sphingosine-1-phosphate phosphatase | Sphn, sphinganine |
| SPT, serine C-palmitoyltransferase | SphnP, sphinganine-1-phosphate |
| | SphP, sphingosine-1-phosphate |
| | TG, triacylglycerol |

Multiple sections 222d may be included within chamber 222 or may be separate from chamber 222 of a device. One or more sections 222d may be located at any location along the flow path of chamber 222 though which nutritional formula travels. In the embodiment of FIG. 2C, nutritional formula may enter from the right or the left of chamber 222, i.e., section 222d may be located upstream or downstream, although it is also considered that section 222d may be located in between one or more of sections 222a, 222b, 222c. While FIG. 2C depicts all three chambers shown in FIG. 2A, plus chamber 222d, it is contemplated that, as described in reference to FIG. 2A, one or more of sections 222a, 222b, 222c may be omitted and/or may contain one or more than one enzyme.

Further, it is also contemplated that chamber 222 may be arranged as shown in FIG. 2B, e.g., section 222d may be included in addition to a single chamber 242 that contains a mixture of enzymes.

As described in reference to FIGS. 2A and 2B, section 222d may be permanently included within a device and/or section 222d may be removable and/or refillable, as described above.

Devices 200, 201, 211 may be configured to treat patients with lipase, protease, and/or amylase or other mineral, vitamin, and/or nutrient deficiencies and/or malabsorption. The devices described herein may be used instead of, or in addition to, other treatments, to provide an increased concentration of hydrolyzed lipids, proteins, and/or carbohydrates in nutritional formula 110. Device 201 may be used as a point-of-care device, e.g., to process a nutritional formula just prior to ingestion, or may be used for bulk generation of processed nutritional formula.

Figure 3:
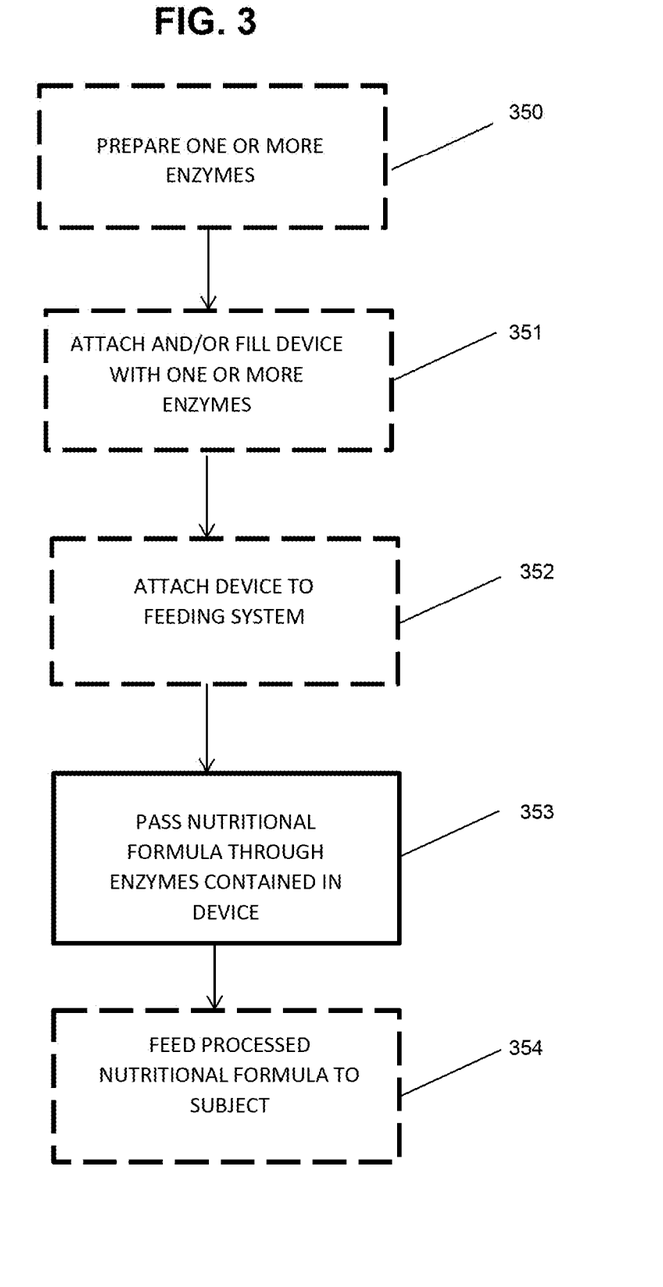
FIG. 3 is a flow chart depicting an exemplary method of using a device, according to embodiments of the present disclosure.

In some aspects, exemplary devices 200, 201, and 211 may be used in the manner shown in FIG. 3. Those of ordinary skill in the art will recognize that one or more steps of the method depicted in FIG. 3 may be omitted or performed out of the order depicted in FIG. 3, or other steps may also be performed.

The first three steps of the method of FIG. 3 are optional, and, depending on the embodiments of device 200, device 201, or device 211 (collectively referred to as 'the device' in reference to FIG. 3), any combination of those steps may be performed, or none of the steps may be performed. First optional step 350 includes preparing one or more enzymes, which may include lipase, protease, and/or amylase. As described above, preparing enzymes may involve mixing, heating, cooling, agitating, immobilizing or otherwise preparing the enzymes for use in the device. Preparation may occur while the enzymes are already contained in the chamber and/or sections of the device, preparation may occur prior to introduction of the nutritional formula 110 into the device, or both. In some embodiments, preparation may include mixing one or more enzymes and/or one or more particles together. Additionally, it is recognized that although step 350 is shown as preceding step 351, which precedes 352, it is understood that these steps may be performed in any order.

Step 351 may include attaching the chamber and/or one or more sections to the device (in embodiments in which the chamber and/or one or more sections is detachable from the device) and/or filling the chamber and/or one or more sections with enzymes, which may include lipase, protease, and/or amylase. In some embodiments, both attaching and filling may occur, while in other embodiments, one (or none) of these may occur. If both actions are taken, the chamber and/or one or more sections may be filled and then attached to the device, while in other embodiments, the chamber and/or one or more sections may be attached to the device and then filled. In some examples, multiple chambers and/or multiple sections may be filled and/or attached to the device.

At step 352, the device may be attached to a feeding system for passing nutritional formula through the device before processed nutritional formula is fed to a subject. For example, the device may be attached to the feeding system of FIG. 1. Indeed, the device may be attached to or otherwise incorporated in any suitable feeding system.

At step 353, nutritional formula 110 may be passed through the enzymes (lipase, protease, and/or amylase) and/or supplement (if included) contained in the device, for example, contained within the one or more chambers or sections of the device. As the nutritional formula passes through the enzymes in the device, the nutritional formula reacts with the enzymes, and the lipids, proteins, and/or carbohydrates in the nutritional formula are hydrolyzed. At step 354, the processed nutritional formula may exit the device. At optional step 354, the processed nutritional formula may be fed to a subject either immediately or after some passage of time. The processed nutritional formula may be fed to a subject in any suitable manner, for example, via a feeding tube, via a drink (e.g., the processed nutritional formula may be added to a beverage), or in any other manner. In some embodiments, devices of the disclosed embodiment may be used so as to prepare bulk amounts of processed nutritional formula, may be used to provide processed nutritional formula at a time before administration of the processed nutritional formula to a subject, and/or for industrial or laboratory preparation.

While many of the embodiments described above relate to devices, including point-of-care devices for processing a nutritional formula, it is also contemplated that lipase, protease, and/or amylase may be added directly to nutritional formula without being contained within a device. For example, lipase, protease, and/or amylase may be added to a nutritional formula (e.g., an individual serving of nutritional formula or a source of nutritional formula) just prior to administration to a person or may be added to a bulk quantity of nutritional formula. The bulk quantity of nutritional formula may be stored, may be divided up and administered to multiple people, and/or may be divided up for multiple rounds of administration to a single person after processing by lipase, protease, and/or amylase.

The added enzymes (lipase, protease, amylase) may be immobilized on one or more solid supports or may be free. If immobilized, each enzyme type may be immobilized separately from one another (i.e., lipase, protease, and amylase may each be immobilized to separate structures or subsets of structures without overlap), or multiple enzyme types may be immobilized on the same structure or structures, or a combination thereof. In some such embodiments, one or more of a valve, frit, mesh, filter, or other mechanical structure, may be used to remove the enzymes—either immobilized or free (i.e., not immobilized) lipase, protease, and/or amylase—from the nutritional formula prior to ingestion of the nutritional formula. For example, free or immobilized enzymes may be mixed into an oral drink and then may be allowed to settle out, or the enzymes may be strained out or otherwise removed, prior to consumption of the oral drink.

In some embodiments, a container (e.g., a beverage holder) may include multiple compartments—one or more compartments for containing nutritional formula, and one or more compartments for containing one or more enzymes. For example, a compartment may contain the nutritional formula, and the lipase, protease, and/or amylase may be stored in a separate compartment or may be distributed among multiple compartments (e.g., lipase, protease, and/or amylase may be stored separately from one another in their own compartments). The enzyme may be free and/or immobilized in the separate compartments. The compartments may be porous or otherwise designed to allow nutritional formula to enter the compartment(s) containing enzyme in order to allow the nutritional formula to interact with the enzyme. Separation of the enzyme into compartments may prevent the enzyme from entering into the nutritional formula when the nutritional formula is removed from the container, e.g., for consumption. In an exemplary embodiment, a beverage container may have a porous compartment within it that permits nutritional formula to flow within the compartment to mix with the enzyme(s) within the compartment. A person may then tip the beverage container to drink the nutritional formula, and the nutritional formula may flow out of the compartment and out of the beverage container, leaving the enzyme within the compartment.

In some aspects, a beverage container may include a porous compartment containing enzyme positioned along an inlet of the beverage container so that nutritional formula poured out of and poured into the container may pass through the compartment and thus be exposed to the lipase, protease, and/or amylase prior to consumption. Again, a person may tip the beverage container to drink the nutritional formula, and the nutritional formula may flow through the compartment and out of the beverage container, leaving the enzyme within the compartment.

While principles of the present disclosure are described herein with reference to illustrative aspects for particular applications, the disclosure is not limited thereto. Those having ordinary skill in the art and access to the teachings provided herein will recognize additional modifications, applications, aspects, and substitution of equivalents that all fall in the scope of the aspects described herein. Accordingly, the present disclosure is not to be considered as limited by the foregoing description.

What is claimed is:

1. A device comprising:
an inlet;
a chamber including a plurality of sections;
immobilized lipase contained within the chamber;
immobilized protease contained within the chamber;
immobilized amylase contained within the chamber;
wherein at least two of the lipase, the protease, and the amylase, are each contained in separate sections of the plurality of sections, and
an outlet, wherein a flow path extends form the inlet, through the chamber, and to the outlet.

2. The device of claim 1, wherein the plurality of sections includes a first section, a second section, and a third section.

3. The device of claim 2, wherein the lipase is contained within the first section, the protease is contained within the second section, and the amylase is contained within the third section.

4. The device of claim 1, wherein the plurality of sections includes a first section and a second section.

5. The device of claim 4, wherein the first section contains at least two of the amylase, the protease, or the lipase.

6. The device of claim 1, further comprising a supplement.

7. The device of claim 6, wherein the supplement includes at least one of a vitamin, a mineral, a nutrient, a medicament, a probiotic, or a prebiotic.

8. The device of claim 6, wherein the supplement is contained in one of the plurality of sections.

9. The device of claim 1, wherein the chamber or one or more of the plurality of sections is removably coupled to the device.

10. The device of claim 1, further comprising a first connector fluidly connected to the inlet and a second connector fluidly connected to the outlet, wherein the first connector and the second connector are dimensioned to connect to a feeding tube.

11. The device of claim 1, wherein at least one of the lipase, the protease, or the amylase is immobilized to a plurality of particles contained within the chamber.

12. The device of claim 1, wherein the plurality of sections are separated by one or more section interfaces.

13. The device of claim 12, wherein the one or more section interfaces are filters.

14. The device of claim 12, wherein the one or more section interfaces allow for the flow of a nutritional formula through the plurality of sections and prevent the flow of the lipase, the protease, and the amylase.

15. A device comprising:
an inlet;
a chamber including a plurality of sections;
lipase contained within the chamber;
protease contained within the chamber;
amylase contained within the chamber,
wherein at least two of the lipase, the protease, and the amylase, are each
contained in separate sections of the plurality of sections; and an outlet, wherein a flow path extends from the inlet, through the chamber, and to the outlet so that a nutritional formula flowing through the device is exposed to the lipase, the protease, and the amylase;

wherein at least one of the lipase, the protease, and the amylase is immobilized within the chamber to a solid structure.

16. The device of claim 15, wherein the solid structure includes a plurality of particles contained within the chamber.

17. The device of claim 15, further comprising at least one of a vitamin, a mineral, a nutrient, a medicament, a probiotic, or a prebiotic.

18. The device of claim 15, wherein the chamber or one or more of the plurality of sections is removably coupled to the device.

19. The device of claim 15, wherein the lipase, the protease, and the amylase are each immobilized within the chamber to one or more solid structures.

20. The device of claim 15, further comprising a first connector fluidly connected to the inlet and a second connector fluidly connected to the outlet, wherein the first connector and the second connector are dimensioned to connect to a feeding tube.

* * * * *

UNITED STATES PATENT AND TRADEMARK OFFICE
CERTIFICATE OF CORRECTION

| | |
|---|---|
| PATENT NO. | : 11,291,236 B2 |
| APPLICATION NO. | : 16/123712 |
| DATED | : April 5, 2022 |
| INVENTOR(S) | : First et al. |

It is certified that error appears in the above-identified patent and that said Letters Patent is hereby corrected as shown below:

In the Claims

In Claim 1, at Column 22, Line 20, delete "form" and insert -- from --.

Signed and Sealed this
Fourteenth Day of June, 2022

*Katherine Kelly Vidal*

Katherine Kelly Vidal
*Director of the United States Patent and Trademark Office*